United States Patent [19]

Löwer et al.

[11] Patent Number: 5,554,656
[45] Date of Patent: Sep. 10, 1996

[54] DISINFECTANT CONCENTRATES AND DISINFECTANTS ON AMINE AND ALCOHOL BASE AND THEIR USE

[75] Inventors: Bernd Löwer; Heinz Eggensperger, both of Hamburg; Peter Goroncy-Bermes, Ahrensburg; Michael Mohr, Kaltenkirehen; Andreas Dettmann, Hamburg, all of Germany

[73] Assignee: Reckitt & Colman Inc., Montvale, N.J.

[21] Appl. No.: 201,610

[22] Filed: Feb. 25, 1994

[30] Foreign Application Priority Data

Feb. 25, 1993 [DE] Germany ............... 43 06 344.6

[51] Int. Cl.⁶ ............... A01N 33/04; A01N 33/06; A01N 33/08

[52] U.S. Cl. ............... 514/674; 514/646; 514/649; 514/654; 514/655; 514/657; 514/659; 514/673; 564/367; 564/368; 564/369; 564/374; 564/391; 564/428; 564/461; 564/462; 564/511; 564/512

[58] Field of Search ............... 564/512, 367, 564/368, 369, 374, 391, 428, 461, 462, 511; 514/674, 646, 649, 654, 655, 657, 659, 673

[56] References Cited

U.S. PATENT DOCUMENTS 4,004,030  1/1977  Schwarzmann ............... 564/512

FOREIGN PATENT DOCUMENTS

| 0333143A2 | 9/1989 | European Pat. Off. ............ C11D 1/65 |
| 0343605 | 11/1989 | European Pat. Off. . |
| 0343605A1 | 11/1989 | European Pat. Off. ........ A01N 33/04 |
| 0385369A2 | 9/1990 | European Pat. Off. ............ C11D 3/00 |
| 2602955 | 2/1988 | France . |
| 2049399 | 3/1972 | Germany . |
| 2263596 | 7/1974 | Germany . |
| 4033272 | 10/1991 | Germany . |
| 0057302 | 4/1983 | Japan . |

OTHER PUBLICATIONS

Chem. Abst. 93–104148 of JP 05043405-A (1993).
EPO Search report dated 27, Apr. 1994 for EP 94250039.

*Primary Examiner*—Peter O'Sullivan
*Attorney, Agent, or Firm*—Frederick H. Rabin; Andrew N. Parfomak; J. Jeffrey Hawley

[57] ABSTRACT

The invention relates to a disinfectant concentrate which contains amine and alcohol wherein the alcohol component includes at least one glycol ether of limited miscibility with water and the amine component includes at least one secondary and/or tertiary alkyl amine free from hydroxyl groups. It also relates to a disinfectant producabile from the disinfectant concentrate, the use of the disinfectant concentrate and of the disinfectant as bactericide, in particular mycobactericide, fungicide or virucide.

16 Claims, No Drawings

DISINFECTANT CONCENTRATES AND DISINFECTANTS ON AMINE AND ALCOHOL BASE AND THEIR USE

FIELD OF THE INVENTION

The invention relates to a disinfectant concentrate based on amine and alcohol, a disinfectant producible from it and their use.

BACKGROUND OF THE INVENTION

Disinfectants are used in many fields where they serve to control micro-organisms. For example, they are used for hand disinfection, operative field or wound disinfection, instrument disinfection, disinfection of surfaces, linen etc. Of great interest is the effectiveness of disinfectants against mycobacteria, in particular against tuberculosis exciters which are relatively resistant, with the result that they are frequently not killed, but merely prevented from reproducing for a short period. Moreover, in addition to the bactericidal effectiveness, the fungicidal and virucidal effectiveness are also of interest. The shortest possible action times of the disinfectants are desirable, with no less thorough and sustained a disinfection effect.

Known thus far are, for example, disinfectants which contain one or more aldehydes or phenols as active ingredients. Furthermore, known from EP 0 333 143 A2 is a liquid cleaning agent which contains a tertiary alkyl amine, particularly N,N-bis-(3-aminopropyl) lauryl amine as biocidal active ingredient and also anionic surfactant as the necessary cleaning component. In addition, this cleaning agent can additionally contain water or alcohols having up to 4 carbon atoms such as methanol, ethanol, etc., as the solvent. It can be used as a disinfectant cleaner.

Also known, from EP 0 343 605 A1, is a tuberculocidal disinfectant which contains N,N-bis-(3-aminopropyl) lauryl amine as the disinfecting component. In addition to a solvent mixture of water and an alcohol having up to 4 carbon atoms such as methanol, ethanol, etc., it can also contain surfactants, quaternary ammonium compounds and complexing agents as cleaning agents.

Known from EP 0 385 369 A2 is a process for the antimicrobial preservation of liquid surfactants and surfactant-containing solutions, in which a preparation containing N,N-bis-(3-aminopropyl) lauryl amine is added to these liquids.

Also known, from DE 40 05 784 A1, is a disinfectant concentrate which contains a cation-active compound and non-ionic surfactant, in addition to a phenoxy alcohol. This concentrate can contain amines or aminopolyols such as tetrabis-(2-hydroxypropyl)N,N,N',N'-ethylene diamine as alkalizing agent.

It is a disadvantage with the aforementioned known disinfectants and disinfectant concentrates that a) disinfectants containing aldehyde and phenol have a relatively strong and unpleasant odor, b) disinfectants based on amine and cation-active compounds or on aromatic alcohols and cation-active compounds attach to surfaces precisely because of their content of cation-active compounds and are incompatible with anionic surfactants since these deactivate them. One disadvantage which all preparations known thus far show is that relatively high active ingredient concentrations are required for achieving an adequate disinfection action within a short period.

It is therefore the object of the invention to provide a disinfectant or a concentrate of the same, whereby the disinfectant has considerably reduced active ingredient concentrations for the same effectiveness, compared with the known disinfectants, or, when it is used, the action time can be substantially reduced to achieve the intended action. The disinfectant and the disinfectant concentrate should distinguish themselves by their lack of odor and be stable and therefore storable over an extended period of time.

SUMMARY OF THE INVENTION

To achieve the above stated object, a disinfectant concentrate or disinfectant has been discovered comprising an alcohol component containing at least one aliphatic glycol ether of limited miscibility with water having 1 to 4 alkylene oxide units and an amine component containing at least one secondary and/or tertiary alkyl amine free from hydroxyl groups. The invention is stable and does not exhibit an undesirable odor and therefore lends itself to storage over an extended period of time.

DETAILED DESCRIPTION OF THE INVENTION

The secondary or tertiary alkyl amine is an amine with the general formula:

(1)

in which $R_1$ is a $C_4$–$C_{20}$, particularly a $C_6$–$C_{18}$ alkyl group, a $C_5$–$C_{10}$, particularly a $C_6$ cycloalkyl group, a $C_7$–$C_{20}$, particularly a $C_7$ arylalkyl group or a $C_6$–$C_{14}$, more particularly a $C_6$ aryl group, and $R_2$ is an aminoalkyl group of the formula —$(CH_2)_n$—$NH_2$, whereby n is a number from 2 to 10, preferably 2 to 6, particularly preferably 2 to 3, and $R_3$ is hydrogen or the same as $R_2$.

Preferably $R_1$ is a $C_6$–$C_{18}$ alkyl group, more preferably a $C_{10}$–$C_{18}$ and particularly preferably a dodecyl, coconut fat alkyl or a tallow fat alkyl group. $R_2$ is preferably an aminopropyl group and $R_3$ is the same as $R_2$ or hydrogen. If $R_2$ and $R_3$ are equal to $C_{12}$ alkyl, the amine is then N-(3-aminopropyl-)-N-dodecyl-1,3-propane diamine or N,N-bis-(3-aminopropyl) lauryl amine which can be obtained under the name "LONZABAC™ 12" from Lonza Ltd., Basel/Switzerland. If $R_2$ and $R_3$ are equal to tallow fat alkyl, then it is an amine which can be obtained under the name "HOE™ S 3119" from Hoechst AG, Frankfurt.

If $R_3$ is hydrogen, $R_1$ is preferably a coconut fat alkyl group and the amine is coconut propylene diamine, which is supplied e.g. by Hoechst under the name GENAMIN™ CCP 100D. The tertiary amine LONZABAC™ 12 is preferred to the secondary amine GENAMIN™ CCP 100D.

The aliphatic glycol ethers of limited miscibility with water are glycol ethers of the general formula $$R_4—(O—R_5)_n—OH, \qquad (2)$$

in which $R_4$ is a straight- or branch-chained alkyl group with 5 to 18 C atoms, preferably 6 C atoms, $R_5$ is a straight- or branch-chained alkyl group with 2 to 4 C atoms, preferably 2 C atoms and n is a whole number between 1 and 4, preferably 2. Hexyl diglycol is particularly preferred.

The glycol ethers according to the invention have in particular a miscibility with water of not more than 10%, preferably up to 5%. In addition, they preferably have a low vapor pressure and a relatively high odor threshold value. The vapor pressure is preferably <0.5 mbar, more preferably <0.3 mbar and the odor threshold value (in water) is preferably >10 mmol/l, more preferably >20 mmol/l. The odor threshold value is defined as the concentration of a substance in air or solvent which just suffices for detecting its typical odor (Lexikon der Biologie, Volume 2, page 228, Herder Verlag, Freiburg, Basel, Vienna (1984)).

In addition to the aforementioned constituents essential to the invention, the disinfectant concentrate or disinfectant can also contain usual additives such as solubilizers, anti-corrosion agents, complexing agents, defoaming agents, stabilizers, buffer, perfume and/or dyes.

The use of the combination according to the invention of glycols of limited miscibility with water and secondary and/or tertiary alkyl amine surprisingly produces a synergistic biocidal effect which permits a lowering of the active ingredient content or a shortening of the action time.

In general, the disinfectant concentrate contains 5 to 50 wt. % sec. and/or tert. amine and 5 to 50 wt. % glycol ether of limited miscibility with water. In particular, it contains 10 to 20 wt. % amine and 20 to 30 wt. % glycol ether.

In general, the ready-to-use disinfectant solution contains 0.1 to 10 wt. % and preferably 1 to 5 wt. % of the disinfectant concentrate and therefore in general 0.005 to 5 wt. % sec. and/or tert. amine and 0.005 to 5 wt. % glycol ether of limited miscibility with water. In particular, it contains 0.025 to 2.5 wt. % amine and 0.025 wt. % glycol ether, whereby 0.1 to 1.0 wt. % amine and 0.2 to 1.5 wt. % glycol ether are preferred.

On using the disinfectant according to the invention, the desired disinfecting action already occurs with action times of 15 minutes. By increasing the use concentration of the concentrate in the working solution, shorter action times are possible. The pH value of prepared working solutions generally lies in the range from 7 to 12, preferably 8 to 11 and particularly preferably 8.5 to 10.5.

The disinfectant concentrate or the disinfectant preferably contains no cation-active compound. Because of the absence of cation-active compounds, there is no danger of the disinfectant's continuing to adhere to a considerable extent to the substrate to be cleaned or attaching to it and not being removed directly and completely by normal rinsing operations.

The active ingredient combination according to the invention can advantageously be combined with anionic and/or non-ionic surfactants, whereby anionic surfactants are preferred as regards cleaning action and non-ionic surfactants as regards the biocidal action. Suitable anionic surfactants include alkyl sulphate, alkyl sulphonate, alkyl ether sulphate, alkyl aryl sulphonate, alkyl ether carboxylic acid and its alkali or ammonium salt, whereby the alkyl group contains 8 to 18 carbon atoms, or a mixture of two or more of these compounds. Preferred is alkyl ether carboxylic acid with 2 to 10, particular 3 to 5 ethylene oxide units.

Through the addition of alkyl ether carboxylic acids in particular, particularly stable disinfectants and disinfectant concentrates result, whereby the disinfectant solutions show high biocidal effectiveness and excellent cleaning activity.

The disinfectant and concentrate according to the invention is a clear solution with very good stability which does not contain a precipitate even after extended storage, so that no active ingredient is lost through sedimentation and use without prior fresh dissolution.

The disinfectants or concentrates according to the invention show good material compatibility with all conceivable substrates to be cleaned.

Also, cleaning effectiveness is already conferred through the surface-active amine component, and can be increased further through the additionally possible content of anionic or non-ionic surfactant. Moreover, there is good rinsability of treated materials.

The biocidal effectiveness for example against *Aspergillus niger, Pseudomonas aeruginosa, Staphylococcus aureus, Proteus vulgaris* or *Candida albicans*, but in particular the effectiveness against mycobacteria, is also obtained at surfaces and instruments.

In particular, the disinfectant concentrate or disinfectant according to the invention are characterized by their low level of emissions, i.e. lack of odor, and a comparatively high flash point.

Compared with concentrates which contain only the secondary and/or tertiary amine or the glycol ether of limited miscibility with water, the disinfectant concentrate according to the invention is characterized by better application properties such as e.g. a lower viscosity and higher storage stability.

The main field of application for the disinfectant concentrate and disinfectant is the control of bacteria, particularly mycobacteria, fungi and viruses.

The invention is further explained but not limited to the following examples.

EXAMPLE 1

Microbiological effectiveness against *Mycobact. terrae* in the germ-carrier test.

The action-increasing effect of the secondary amine GENAMIN™ CCP 100 D and of the tertiary amines LONZABAC™ 12 and HOE™ S 3119 mixed with a glycol ether of limited miscibility with water, taking hexyl diglycol as an example, is made clear by testing this mixture in the test arrangement of the germ-carrier test against *Mycobacterium terrae* according to DGHM.

The action times required until the germ carriers are germ-free are noted.

|  | 0.5% | 1.0% | 2.0% | 3.0% | 5.0% |
|---|---|---|---|---|---|
| Formulation A | | | | | |
| 20 g MARLIPAL ™ 013/120* | >120' | >120' | >120' | >120' | >120' |
| 6 g LUTENSOL ™ ON 110* | | | | | |
| g Hexyl diglycol | | | | | |
| to 100 g water, purified | | | | | |
| Formulation B | | | | | |
| 20 g MARLIPAL ™ 013/120 | >60' | 30' | 15' | 15' | 15' |
| 6 g LUTENSOL ™ ON 110 | | | | | |
| 20 g Hexyl diglycol | | | | | |
| 12 g GENAMIN ™ CCP 100 D | | | | | |
| to 100 g water, purified | | | | | |
| Formulation C | | | | | |
| 20 g MARLIPAL ™ 013/120 | 120' | 120' | 60' | 30' | 3'0 |

-continued

|  | 0.5% | 1.0% | 2.0% | 3.0% | 5.0% |
|---|---|---|---|---|---|
| 6 g LUTENSOL ™ ON 110 |  |  |  |  |  |
| 20 g Hexyl diglycol |  |  |  |  |  |
| 12 g LONZABAC ™ 12 |  |  |  |  |  |
| to 100 g water, purified |  |  |  |  |  |
| Formulation D |  |  |  |  |  |
| 20 g MARLIPAL ™ 013/120 | >120' | 120' | 120' | 120' | 60' |
| 6 g LUTENSOL ™ ON 110 |  |  |  |  |  |
| 20 g Hexyl diglycol |  |  |  |  |  |
| 12 g HOE ™ S 3119 |  |  |  |  |  |
| to 100 g water, purified |  |  |  |  |  |

*MARLIPAL ™ 013/120 = Tridecane polyethylene glycol (12) ether
*LUTENSOL ™ ON 110 = Isodecane polyethylene glycol (11) ether

EXAMPLE 2

Quantitative suspension test according to DGHM with 0.2% albumin as serum charge with *Ps. aeruginosa* (I) and *Staph. aureus* (II)

TABLE 2

| Action time | Conc. [%] | Formulation E (amine only) | Formulation F (amine + glycol ether) | Formulation G (glycol ether only) |
|---|---|---|---|---|
| (I) 30 min | 0.5 | 0.94 | 1.17 | 0 |
|  | 1.0 | 1.30 | 1.42 | 0 |
|  | 3.0 | 1.95 | 2.00 | 0 |
|  | 5.0 | 3.43 | 3.69 | 0 |
| 60 min | 0.5 | 3.55 | 4.30 | 0 |
|  | 1.0 | 4.67 | 4.48 | 0 |
|  | 3.0 | 5.08 | 5.08 | 0 |
|  | 5.0 | 4.78 | ≧5.08 | 0 |
| (II) | 0.5 | 3.39 | 5.53 | 0 |
|  | 1.0 | 4.30 | ≧5.38 | 0 |
|  | 3.0 | ≧5.38 | ≧5.38 | 0 |
|  | 5.0 | ≧5.38 | ≧5.38 | 0 |

The logarithmic germ-count induction factors are noted.

Formulations of examples 2 and 3

|  | E | F | G | H | I |
|---|---|---|---|---|---|
| LONZABAC ™ 12 | 12% | 12% | — | — | — |
| GENAMIN ™ CCP 100 D | — | — | — | 12% | 12% |
| Hexyl diglycol | — | 20% | 20% | 20% | 20% |
| MARLIPAL ™ 13/120 | 30% | 20% | 20% | 20% | 20% |
| LUTENSOL ™ ON 110 | 6% | 6% | 6% | 6% | 6% |
| Water | 62% | 42% | 54% | 42% | 62% |

Formulation F corresponds to C from Example 1
Formulation G corresponds to A from Example 1
Formulation H corresponds to B from Example 1

EXAMPLE 3

The test arrangement is the same as in Example 2. *Ps. aeruginosa* is used as test germ. The activity time is short.

| Action time | Conc. [%] | Formulation G (glycol ether only) | Formulation H (amine + glycol ether) | Formulation I (amine only) |
|---|---|---|---|---|
| 5 min | 0.5 | 0 | 1.02 | 0.76 |
|  | 1.0 | 0 | 1.22 | 0.78 |

-continued

| Action time | Conc. [%] | Formulation G (glycol ether only) | Formulation H (amine + glycol ether) | Formulation I (amine only) |
|---|---|---|---|---|
|  | 3.0 | 0 | 3.42 | 0.78 |
|  | 5.0 | 0 | ≧5.23 | 0.81 |

The increase in action through the addition of the glycol ether of limited miscibility with water is particularly clear in the studies with *Pseudomonas aeruginosa*—especially in the lower concentration range and with short action times (Example 3). *Staphylococcus aureus* is already relatively sensitive towards the basic mixture; however, an increase in the germ reduction is achieved through addition of the glycol ether with short times and low concentrations.

We claim:

1. A disinfectant composition concentrate comprising: at least one aliphatic glycol ether according to the general formula:

$$R_4-(O-R_5)_n-OH$$

in which:

$R_4$ is a straight- or branch-chained alkyl group having 5 to 18 C atoms;

$R_5$ is a straight- or branch-chained alkyl group having 2 to 4 C atoms; and, n is a whole number between 2 and 4, of limited miscibility with water and;

at least one alkyl amine according to the general formula:

$$R_1-N\begin{matrix}R_2\\ \\R_3\end{matrix}$$

in which $R_1$ is a $C_4$–$C_{20}$ alkyl group, a $C_5$–$C_{10}$ cycloalkyl group, a $C_7$–$C_{10}$ aryl alkyl group, or a $C_6$–$C_{14}$ aryl group;

$R_2$ is an amino alkyl group of the formula $-(CH_2)_n-NH_2$, wherein n is a number from 2 to 10; and, $R_3$ is hydrogen or the same as $R_2$.

2. A composition according to claim 1 wherein $R_1$ is a $C_6$–$C_{18}$ alkyl group, a $C_6$ cycloalkyl group, a $C_7$ aryl alkyl group, or a $C_6$ aryl group; $R_2$ is an amino alkyl group of the formula $-(CH_2)_n-NH_2$ whereby n is a number from 2 to 3.

3. A composition according to claim 2 wherein $R_1$ is a dodecyl, coconut fat alkyl or a tallow fat alkyl group.

4. A composition according to claim 1 wherein $R_4$ is a straight- or branch-chained alkyl group having 6 C atoms, $R_5$ is an alkyl group having 2 C atoms and n is 2.

5. A composition according to claim 4 wherein the glycol ether has a water miscibility of not more than 10%, a vapor pressure of <0.5 mbar and an odor threshold value (in water) to >10 mmol/l.

6. A composition according to claim 5 wherein said glycol ether has a water miscibility of not more than 5%, a vapor pressure of <0.5 mbar, and an odor threshold value (in water) of >20 mm/l.

7. A composition according to claim 1 wherein said composition further comprises an anionic surfactant containing an alkyl sulphate, an alkyl sulphonate, an alkyl ether sulphate, an alkyl aryl sulphonate, an alkyl ether carboxylic acid and its alkali or ammonium salt, wherein said alkyl groups contain 8 to 18 carbon atoms, or a mixture of two or more of these compounds.

8. A composition according to claim 7 wherein said anionic surfactant is an alkyl ether carboxylic acid having from 3 to 5 ethylene oxide units.

9. A composition according to claim 8 wherein said aliphatic glycol ether is hexyl diglycol.

10. A composition according to claim 1 wherein said aliphatic glycol ether is hexyl diglycol.

11. A composition according to claim 10 wherein for said alkyl amine said $R_1$ is a dodecyl, coconut fat alkyl, or a tallow fat alkyl group.

12. A composition according to claim 1 wherein for said alkyl amine said $R_1$ is a dodecyl, coconut fat alkyl, or a tallow fat alkyl group.

13. A disinfectant composition according to claim 1 wherein said composition is an aqueous dilution of the disinfectant concentrate.

14. A composition according to claim 4 wherein said concentrate is present in an amount of from about 0.1 to 10 wt. %.

15. A composition according to claim 1 wherein said composition has a pH value of 7 to 12.

16. A method of using the composition according to claim 1 as bactericide, mycobactericide, fungicide or virucide.

* * * * *